United States Patent
Collins (10) Patent No.: US 9,622,755 B2
(45) Date of Patent: Apr. 18, 2017

(54) SURGICAL CUTTING BLOCK (71) Applicant: Zimmer, Inc., Warsaw, IN (US)

(72) Inventor: James S. Collins, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 257 days.

(21) Appl. No.: 13/726,765

(22) Filed: Dec. 26, 2012

(65) Prior Publication Data
US 2014/0180294 A1 Jun. 26, 2014

(51) Int. Cl.
*A61B 17/15* (2006.01)

(52) U.S. Cl.
CPC .......... *A61B 17/157* (2013.01); *A61B 17/155* (2013.01)

(58) Field of Classification Search
CPC .................................................... A61F 2/4657
USPC ................................ 606/79–85, 86 R, 87–98
See application file for complete search history.

(56) References Cited

U.S. PATENT DOCUMENTS

| 2,692,748 | A | * | 10/1954 | Anderson | B01L 9/00 126/30 |
| 5,213,112 | A | * | 5/1993 | Niwa et al. | 600/587 |
| 2003/0073998 | A1 | * | 4/2003 | Pagliuca | A61B 17/0218 606/86 A |
| 2004/0122441 | A1 | * | 6/2004 | Muratsu | 606/102 |
| 2007/0027418 | A1 | * | 2/2007 | Calco | A61F 5/055 602/18 |

* cited by examiner

*Primary Examiner* — Samuel Hanna
(74) *Attorney, Agent, or Firm* — Schwegman Lundberg & Woessner, P.A.

(57) ABSTRACT

Tools or other instruments can be used by a surgeon to complete an orthopedic procedure. One tool can include a reference block and a cutting block coupled to the reference block via an adjuster. The reference block can include a body portion and a depth arm having at least one longitudinal groove extending along a side surface. The adjuster can be coupled to the cutting block and configured to move the cutting block along the depth arm. The adjuster can include a roller having an elongate body, the roller including at least one circular guide member and a turn knob positioned along the elongate body, and a resilient member having a base and at least one leg extending from the base, where the adjuster is configured to couple the cutting block to the depth arm.

14 Claims, 6 Drawing Sheets

SURGICAL CUTTING BLOCK

BACKGROUND

Tools or other instruments can be used by a surgeon to complete an orthopedic procedure. For example, a surgical cutting system can be used during an orthopedic procedure to prepare a bone for a prosthetic implant.

SUMMARY

The present disclosure is directed to surgical cutting block systems and methods for the placement of a cutting block on a bone during an orthopedic procedure. Using the surgical cutting block systems and methods of the present disclosure, a surgeon can quickly and easily position the cutting block at a particular depth and a particular varus/vagus angle. Additionally, the surgical cutting block system of the present disclosure can be quickly and easily cleaned.

The present inventors have recognized, among other things, that existing systems and methods for adjusting a depth of a cutting block fail to provide a surgeon with certain ease of use features, such as adjustability and cleanability. For example, existing systems and methods can include a rack and pinion type of linear actuator that can include a pair gears. Each gear can include "teeth" that can engage each other to adjust the cutting block depth. However, actuators including "teeth" gears can be expensive to manufacture and can be difficult to clean, as material can get trapped between the "teeth" of the gears.

The present systems and methods provide or use a reference block, a cutting block, and an adjuster. The reference block can include a body portion and a depth arm. The depth arm can extend from the body portion and having at least one longitudinal groove extending along a side surface. The cutting block can have a bore configured to receive the depth arm. The adjuster can be coupled to the cutting block and configured to move the cutting block along the depth arm. The adjuster can include a roller having an elongate body, where the roller can include at least one circular guide member and a turn knob positioned along the elongate body. The adjuster can further include a resilient member having a base and at least one leg extending from the base, where the adjuster is configured to couple the cutting block to the depth arm.

To better illustrate the surgical cutting block systems and methods disclosed herein, a non-limiting list of examples is provided here:

In Example 1, a system, comprises a reference block including a body portion and a depth arm, the depth arm extending from the body portion and having at least one longitudinal groove extending along a side surface, a cutting block having a bore configured to receive the depth arm, and an adjuster coupled to the cutting block and configured to move the cutting block along the depth arm. The adjust comprises a roller having an elongate body, the roller including at least one circular guide member and a turn knob positioned along the elongate body, and a resilient member having a base and at least one leg extending from the base, wherein the adjuster is configured to couple the cutting block to the depth arm.

In Example 2, the system of Example 1 is optionally configured such that the cutting block includes an opening configured to receive the roller such that the at least one circular guide member is positioned within the at least one longitudinal groove. The at least one circular guide member is configured to rotate within the at least one longitudinal groove, when the turn knob is rotated, to move the cutting block along the depth arm.

In Example 3, the system of any one or any combination of Examples 1 or 2 is optionally configured such that the base includes at least one aperture configured to receive a fastener to couple the resilient member to the cutting block.

In Example 4, the system of any one or any combination of Examples 1-3 is optionally configured such that the at least one leg includes an extender portion and a spacer portion. The spacer portion configured to contact the elongate body of the roller, and the extender portion located between the spacer portion and the base.

In Example 5, the system of Example 4 is optionally configured such that when the resilient member includes a first leg and a second leg and the roller includes a first circular guide member and a second circular guide member, the spacer portion of the first leg and the spacer portion of the second leg contact the elongate body of the roller such that the first and second circular guide members are positioned between the respective spacer portions of the first and second leg.

In Example 6, the system of Example 4 is optionally configured such that the spacer portion has a first thickness and the extender portion has a second thickness, the first thickness greater than the second thickness.

In Example 7, the system of Example 6 is optionally configured such that the thickness of the spacer portion is sufficient to provide a gap between a side wall of the cutting block and the extender portion.

In Example 8, the system of Example 7 is optionally configured such that the gap is at least approximately 0.5 millimeters.

In Example 9, the system of any one or any combination of Examples 1-8 is optionally configured such that the at least one circular guide member has a first hardness and the depth arm has a second hardness, the first hardness different from the second hardness.

In Example 10, the system of Example 9 is optionally configured such that the first hardness is greater than the second hardness.

In Example 11, the system of Example 9 is optionally configured such that the first hardness is less than the second hardness.

In Example 12, the system of any one or any combination of Examples 1-11 is optionally configured such that the at least one longitudinal groove is a square groove in groove depth and groove width.

In Example 13, the system of any one or any combination of Examples 1-12 is optionally configured such that the at least one longitudinal groove includes a first surface and a second surface, the first surface and the second surface being substantially parallel to each other.

In Example 14, the system of Example 13 is optionally configured such that the first surface has a first length and the second surface has a second length, the first length being equal to or greater than the second surface.

In Example 15, the system of Example 13 is optionally configured such that the at least one circular guide member includes a first surface configured to be adjacent to the first surface of the at least one longitudinal groove and a second surface configured to be adjacent to the second surface of the at least one longitudinal groove.

In Example 16, the system of Example 15 is optionally configured such that the first surface of the at least one circular guide member is substantially perpendicular to a longitudinal axis of the roller and the second surface of the at least one circular guide member forms an oblique angle relative to the longitudinal axis.

In Example 17, the system of Example 16 is optionally configured such that when the roller includes a first circular guide member and a second circular guide member, the angled surface of the first circular guide member and the angled surface of the second circular guide member form an inclusive angle of approximately 7 degrees 20 minutes.

In Example 18, a system comprises a reference block, and a cutting block, coupled to the reference block, having a slot, configured for guiding a cutting tool, and an adjuster, configured for moving the cutting block with respect to the reference block. The adjuster comprises a roller having an elongate body, the roller including at least one circular guide member, and a turn knob, the at least one circular guide member and the turn knob positioned along the elongate body, and a resilient member configured to apply a force to the roller. The resilient member including a base, and at least one leg extending from the base, and a fastener configured to couple the resilient member to the cutting block.

In Example 19, the system of Example 18 is optionally configured such that the reference block includes a body portion and a depth arm, the depth arm extending from the body portion and having at least one longitudinal groove extending along a side surface.

In Example 20, the system of Example 19 is optionally configured such that the cutting block further includes a bore configured to receive the depth arm and an opening configured to receive the roller, and wherein the roller is configured to, when rotated, move the cutting block along the depth arm.

In Example 21, the system of any one or any combination of Examples 18-20 is optionally configured such that the at least one leg includes an extender portion and a spacer portion, the spacer portion configured to contact the elongate body of the roller, and the extender portion location between the spacer portion and the base.

In Example 22, the system of claim 21 is optionally configured such that the spacer portion has a first thickness and the extender portion has a second thickness, the first thickness greater than the second thickness.

In Example 23, the system of any one or any combination of Examples 18-22 is optionally configured such that the at least one circular guide member has a first hardness and the depth arm has a second hardness, the first hardness different from the second hardness.

In Example 24, the system of any one or any combination of Examples 18-23 is optionally configured such that the at least one longitudinal groove include a first surface having a first length and a second surface having a second length, the first length being equal to or greater than the second surface.

In Example 25, the system of any one or any combination of Examples 18-24 is optionally configured such that the at least one circular guide member includes a first surface adjacent to the first surface of the at least one longitudinal groove and a second surface adjacent to the second surface of the at least one longitudinal groove.

In Example 26, the system of claim 25 is optionally configured such that the first surface of the at least one circular guide member is substantially perpendicular to a longitudinal axis of the roller and the second surface of the at least one circular guide member forms an oblique angle relative to the longitudinal axis of the roller.

In Example 27, a method comprises sliding a system including a reference block, having a depth arm including a longitudinal groove, and a cutting block having an adjuster, the adjuster including an elongate body having a turn knob and a circular guide member positioned along the elongate body, over an intramedullary rod. The method can include applying a rotational force to the turn knob to adjust a cutting depth of the cutting block, wherein the circular guide member rotates within the longitudinal groove in response to the rotational force.

In Example 28, the method of Example 27 is optionally configured to further include adjusting the reference block with respect to the intramedullary rod to adjust a varus/valgus angle of the cutting block; and coupling the reference block to the intramedullary rod.

In Example 29, the method of Example 28 is optionally configured to further include coupling the cutting block to a bone at a particular depth and a particular varus/valgus angle, and removing the reference block from the cutting block.

These and other examples and features of the present surgical cutting block systems and methods will be set forth in part in the following Detail Description. This Summary is intended to provide an overview of the present subject matter; it is not intended to provide an exclusive or exhaustive explanation. The Detailed Description is included to provide further information about the present surgical cutting block systems and methods.

BRIEF DESCRIPTION OF THE DRAWINGS

In the drawings, which are not necessarily drawn to scale, like numerals can be used to describe similar components in different views. The drawings illustrate generally, by way of example, but not by way of limitation, various embodiments discussed in the present patent document.

DETAILED DESCRIPTION

Figure 1:
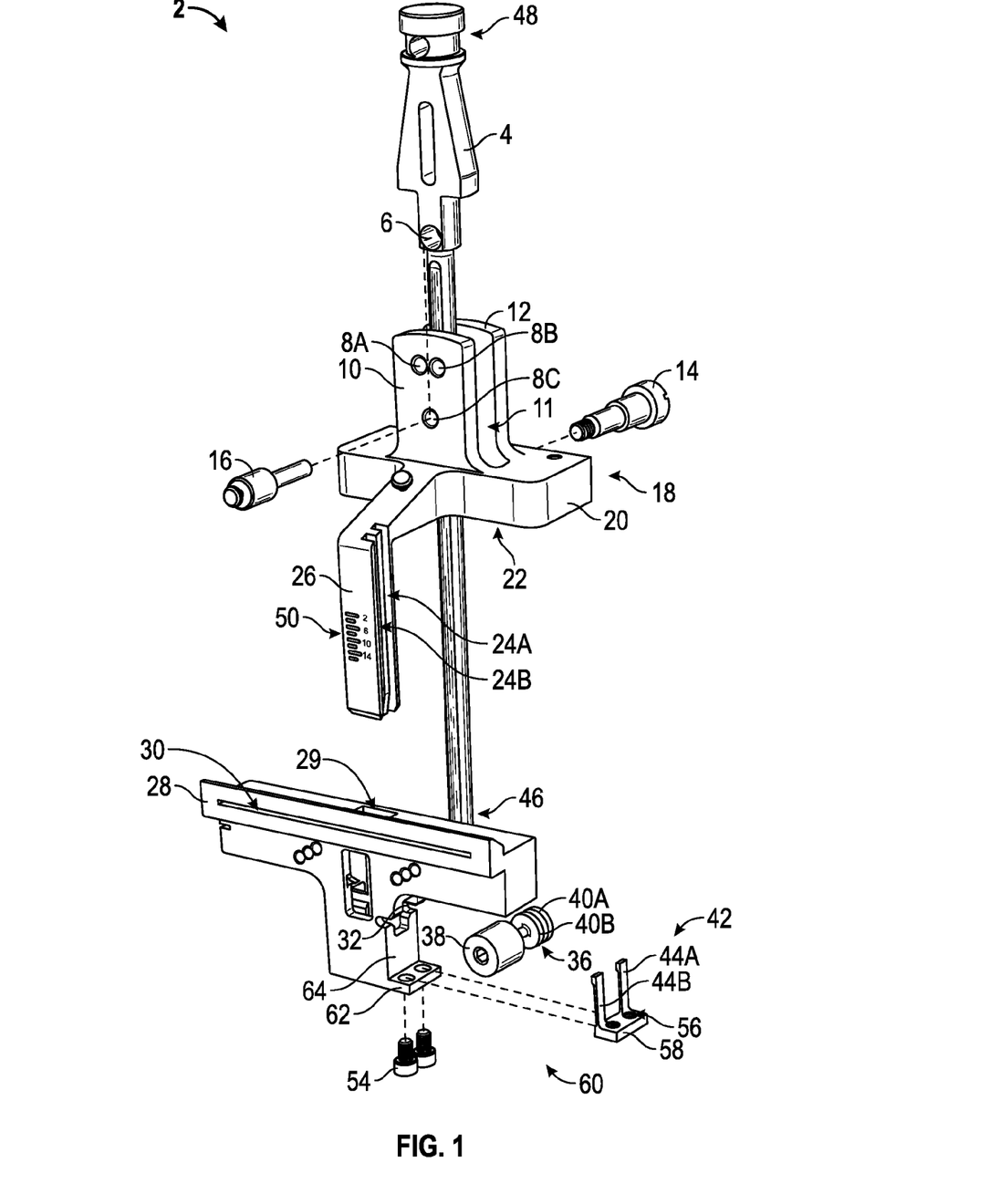
FIG. 1 illustrates an exploded view of a system, in accordance with at least one example of the present disclosure.

FIG. 1 illustrates a perspective view of a system 2, in accordance with at least one example of the present disclosure. The system 2, according to the present disclosure, can be used to position a cutting block 28 at a particular depth and at a particular varus/valgus angle on a bone during an orthopedic procedure. For example, the system 10 can be used to prepare a distal end of a femur or a proximal end of a tibia for a knee arthroplasty procedure, a proximal end of a femur for a hip arthroplasty procedure, or a proximal end of a humerus for a shoulder arthroplasty procedure.

The system can include a reference block 18, a cutting block 28, and an adjuster 60. The cutting block 28 can be coupled to the reference block 18 via the adjuster 60. The adjuster 60 can enable the cutting block 28 to move along the reference block 18 to adjust the cutting depth of the cutting block 28. The reference block 18 can include a body portion 20 and a depth arm 26. The body portion 20 can include a bone contacting surface 22 configured to contact a distal end of a bone during an orthopedic procedure. The reference block 18 can include a depth arm 26 extending from the body portion 20. The depth arm 26 can include a first longitudinal groove 24A and a second longitudinal groove 24B extending along a side surface 27 of the depth arm 26 (hereinafter generically referred to "longitudinal groove 24" or collectively as "longitudinal grooves 24"). In the example of FIG. 1, the depth arm 26 includes a first longitudinal groove 24A and a second longitudinal groove 24B; however, the depth arm 26 can include more or less than two longitudinal grooves 24.

The reference block 18 can include a bore 11 extending through the body portion 20 of the reference block 18. The bore 11 can be configured to receive an intramedullary rod or nail 4. The intramedullary rod or nail 4 can include a first end 46 configured to be inserted into an intramedullary canal and a second end 4 configured to extend beyond the distal end of a bone. The reference block 18 can include a primary locking hole (not shown) configured to receive a locking pin 14 that can rotatably the reference block 18 to the intramedullary rod or nail 4.

As illustrated in FIG. 1, a first member 10 and a second member 12 can extend from the body portion 20. The first and second members 10, 12 can extend in a direction opposite of the depth arm 26. The first member 10 can include a plurality of varus/valgus guide holes 8A-8C (hereinafter generically referred to "guide hole 24" or collectively as "guide holes 8") that can adjust the varus/valgus angle of the cutting block 2. Each varus/valgus guide hole 8 can represent a varus/valgus angle. For example, varus/valgus guide hole 8C can represent a minimum varus/valgus angle, varus/valgus guide hole 8A can represent a maximum left varus/valgus angle, and varus/valgus guide hole 8B can represent a maximum right varus/valgus angle. The varus/valgus guide holes 8 can be configured to receive locking pin 16 to secure the cutting block 28 at a particular varus/valgus angle.

The cutting block 28 can include a slot 30 to guide one or more cuts to be made by a cutting instrument, such as a saw, to remove a portion of a bone. The cutting block 28 can include a bore 29 configured to receive the depth arm 26. The cutting block 28 can be operatively coupled with the adjuster 60 such that the adjuster 60 can effectuate movement of the cutting block 28 along the depth arm 26, thereby adjusting the cutting depth of the slot 30 with respect to the bone.

The adjuster 60 can include a roller 36 having an elongate body 72. The roller 60 can include a first circular guide member 40A and a second circular guide member 40B (hereinafter generically referred to "circular guide member 40" or collectively as "circular guide members 40"). In the example of FIG. 1, the roller 60 includes two circular guide members 40; however, the adjuster 60 can include more or less than two circular guide members 40. In an example, the number of longitudinal grooves 24 can equal the number of circular guide members 40. The circular guide members 40 can be configured to be positioned within the longitudinal grooves 24. When the turn knob 38 is rotated, the circular guide members 40 can rotate within the longitudinal grooves 24 to convert the rotational movement into linear motion and move the cutting block 28 along the depth arm 26, thereby adjusting the cutting depth of the slot 40.

The adjuster 60 can include a resilient member 42 having a base 58 and a first leg 44A and a second leg 44B extending from the base 58 (hereinafter generically referred to "leg 44" or collectively as "legs 44"). In the example of FIG. 1, the roller 60 includes two legs 4; however, the resilient member 42 can include more or less than two legs 44. The resilient member 42 can be configured to couple the cutting block 28 to the depth arm 26. For example, the resilient member 42 can apply a force to the depth arm 26 via the roller 36 to couple the cutting block 28 to the depth arm 26.

The cutting block 28 can include a plate portion 62 that can be configured to receive the base 58 of the resilient member 42. The plate portion 62 can include one or more apertures 63 that can correspond to one or more apertures 56 in the base 58. One or more fasteners 54 (e.g., screws) can interact with the apertures 56 in the plate portion 62 and the apertures 58 of the base, thereby coupling the adjuster 60 to the cutting block 28.

The cutting block 28 can include an opening 32 in a side surface 62 configured to receive the roller 36. The opening 32 can be in fluid communication with the bore 29 of the cutting block 28 such that, when assembled, the circular guide members 40 can be positioned within the longitudinal grooves 24. When the turn knob 38 is rotated, the circular guide members 40 can rotate within the longitudinal grooves 24 to move the cutting block 28 along the depth arm 26.

The cutting block 28 can be coupled to the reference block 18 via a friction fit between the longitudinal grooves 40 and the circular guide member 40. For example, the legs 44 can apply a force to the elongate body 72 that can create friction between the longitudinal grooves 24 and the circular guide members 40. The friction can be sufficient to maintain the cutting block 28 in position along the depth arm 26, for example, when the depth arm 26 is positioned vertically. In an example, the friction fit between the circular guide members 40 and the longitudinal grooves 24 is sufficient such that the cutting block 28 does not move with only gravitational forces acting on the cutting block 28. The cutting block 28 can move along the depth arm when a force is applied. For example, when a rotational force is applied to the roller 36 (e.g., by turning the turn knob 38), the cutting block 28 can move along the depth arm 26.

Figure 2:
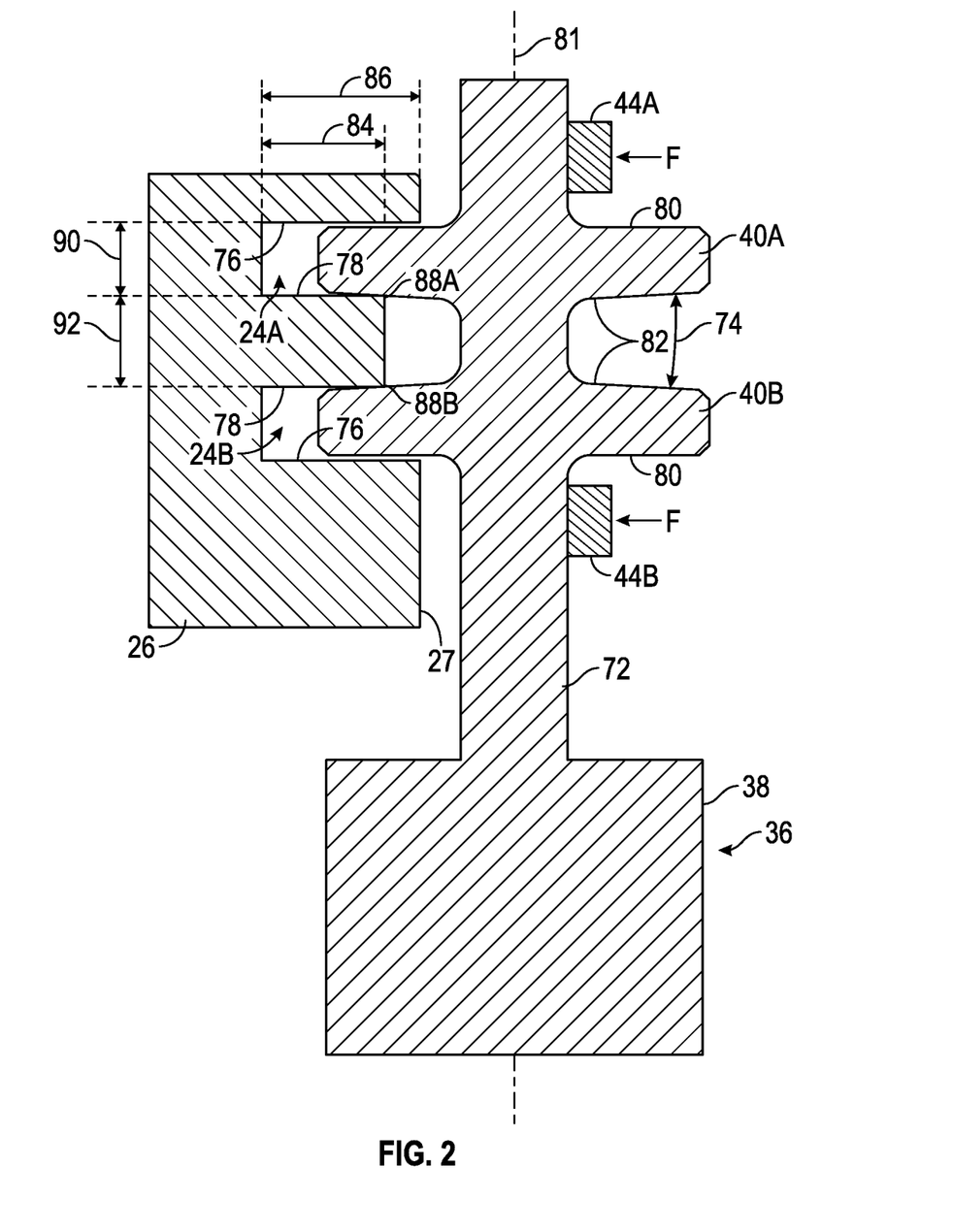
FIG. 2 illustrates a cross-sectional view of a depth arm, a roller, and legs, in accordance with at least one example of the present disclosure.

FIG. 2 illustrates a cross-sectional view of a depth arm 26, the roller 36, and the legs 44, in accordance with at least one example of the present disclosure. In the example of FIG. 2, the elongate body 72 can be positioned substantially parallel to the side surface 27 of the depth arm 26. The first longitudinal groove 24A can receive the first circular guide member 44A and the second longitudinal groove 24B can receive the second circular guide member 44B. As discussed herein, the legs 44 can provide a force "F" onto the roller 36 to provide a friction fit between the longitudinal grooves 24 and the circular guide members 40.

In an example, a hardness of the circular guide members 44 and a hardness of the depth arm 26 are different. For example, the circular guide members 44 can have a first hardness and the depth arm 26 can have a second hardness, where the first hardness is different form the second hardness. In an example, the first hardness can be greater than the second hardness. In another example, the second hardness can be greater than the first hardness.

The hardness can be measured using a Rockwell "C" scale. When the first hardness of the circular guide members 44 is greater than the second hardness of the depth arm 26, the first hardness can be within a range of from about 53 to about 57 on a Rockwell "C" scale and the second hardness can be within a range of form about 38 to 48 on a Rockwell "C" scale. When the first hardness of the circular guide members 44 is less than the second hardness of the depth arm 26, the first hardness can be within a range of from about 38 to about 48 on a Rockwell "C" scale and the second hardness can be within a range of form about 53 to 57 on a Rockwell "C" scale. In an example, 440 A stainless steel can be used as a material that can provide a Rockwell "C" hardness of about 53 to 57. Additionally, 17-4 stainless steel can be used as a material that can provide a Rockwell "C" hardness of about from 38 to 47.

The longitudinal grooves 24 can be square grooves. The longitudinal grooves 24 can include a first surface 76 and a second surface 78 configured to be parallel to each other. In an example, the first surface 76 can have a length 86 that is equal to, greater, or less than a length 84 of the second surface 78. In the example of FIG. 2, the length 86 of the first surface 76 is greater than the length 84 of the second surface 84. The length 86 can be greater than the length 84 to assist in stabilizing the circular guide members 40 within the longitudinal grooves 24. A thickness 90 of the longitudinal grooves 24 can be sufficient such that the longitudinal grooves 24 can receive the circular guide members 40.

The circular guide members 40 can include a first surface 80 configured to be adjacent to the first surface 76 the longitudinal grooves 24 and a second surface 82 configured to be adjacent to the second surface 78 of the longitudinal grooves 24. Additionally, the first surface 80 of the circular guide members 40 can be parallel to the first surface 76 of the longitudinal grooves 24. The first surface 80 of the circular guide members 40 can be substantially perpendicular to a longitudinal axis 81 of the roller 38.

The second surface 82 of the circular guide members 40 can be an angled to form an oblique angle relative to the longitudinal axis 81. The second surface 82 of the circular guide members 40 can form an oblique angle such that edges 88A and 88B (collectively referred to as "edges 88") of the second surfaces 78 of the longitudinal grooves 24 can contact the circular guide members 40. In an example having the first circular guide member 44A and the second circular guide member 44B, the second surface 82 of the first and second circular guide members 40 can form an oblique angle with respect to a plane that is perpendicular to the longitudinal axis 81. In an example, the second surface 82 of the first and second circular guide members 40 can form an oblique angle within a range of from 3 to about 10 degrees. In an example, the oblique angle can be approximately 7 degrees. Other oblique angles can be used and can be based on factors, such as the thickness 92 between the longitudinal grooves 24. While not shown in FIG. 2, the first surfaces 80 of the circular guide members 40 can form the oblique angle and the second surfaces 82 can be substantially perpendicular to the longitudinal axis 81. Additionally, both the first surfaces 80 and the second surfaces 82 can be angled to form an oblique angle with respect to the longitudinal axis 81.

A thickness 92 between the second surfaces 78 of the longitudinal grooves 24 can be sufficient such that the edges 88 contact a point along a surface of the circular guide member 44. In an example, the point where the edges 88 contact the surface of the circular guide members 40 can be approximately a midpoint between the elongate body 72 and an outer-most end of the circular guide members 40. The edges 88 contacting the circular guide members 40 at the midpoint can provide leeway for wear. For example, over time, if the circular guide members 40 wear, the edges 88 can continually contact a point along the surface of the circular guide members 40.

The legs 44 can provide a force "F" to the elongate member 72 to create friction between the circular guide members 40 and edges 88 of the longitudinal grooves 24. The direction of the force "F" can be substantially perpendicular to the longitudinal axis 81. The legs 44 can compress onto the elongate body 72 to create a force. For example, the edges 88 can engage with the circular guide members 40.

Rotational movement of the turn knob 38 can effectuate movement of the cutting block 28 and adjust the cutting depth of the slot 30 with respect to the bone. As the turn knob 28 is rotated, the circular guide members 40 can rotate within the longitudinal grooves 24 and adjust the cutting depth of the slot 30.

Figure 3A:
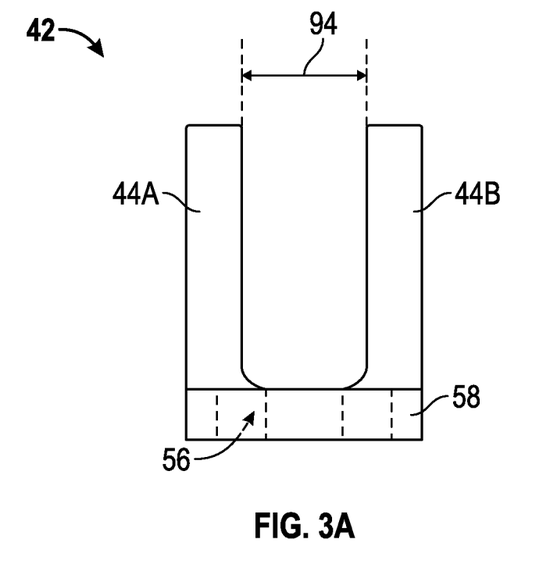
FIG. 3A illustrates a front view of a resilient member, in accordance with at least one example of the present disclosure.

FIG. 3A illustrates a front view of a resilient member 42, in accordance with at least one example of the present disclosure. As illustrated in FIG. 3A, the base 56 can include the apertures 56 configured to align with corresponding apertures 63 in the cutting guide 28 and receive the fasteners 54 to couple the resilient member 42 to the cutting block 30. The resilient member 42 can include a space 94 between the first leg 44A and the second leg 44B. The first leg 44A and the second leg 44B can contact the elongate body 72 of the roller 36 such that the circular guide members 40 are positioned within the space 94, as illustrated in FIG. 4A.

Figure 3B:
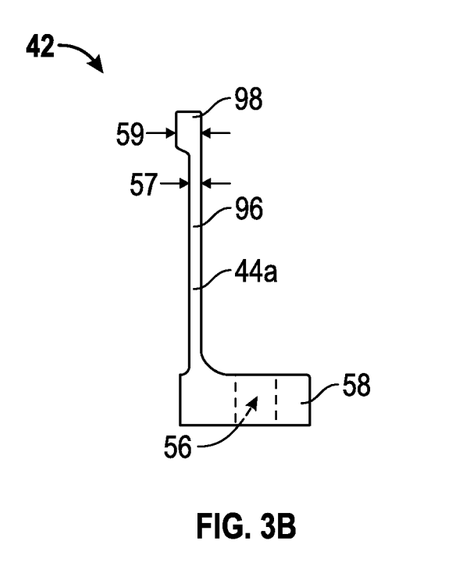
FIG. 3B illustrates a side view of the resilient member of FIG. 3A, in accordance with at least one example of the present disclosure.

FIG. 3B illustrates a side view of the resilient member 42 of FIG. 3A, in accordance with at least one example of the present disclosure. The legs 44 can include an extender portion 96 and a spacer portion 98. The spacer portion 98 can be configured to contact the elongate body 72 of the roller 36. The spacer portion 98 can have a thickness 59 that is greater than a thickness 57 of the extender portion 96. The thickness 57 of the extender portion 96 can be within a range of from about 0.36 millimeters to about 1.27 millimeters. In an example, the thickness 57 of the extender portion 96 can be about 0.76 millimeters. The thickness 59 of the spacer portion 98 can be within a range of from about 0.76 millimeters to about 2.54 millimeters. In an example, the thickness 59 of the spacer portion 98 can be about 1.52 millimeters.

Figure 4A:
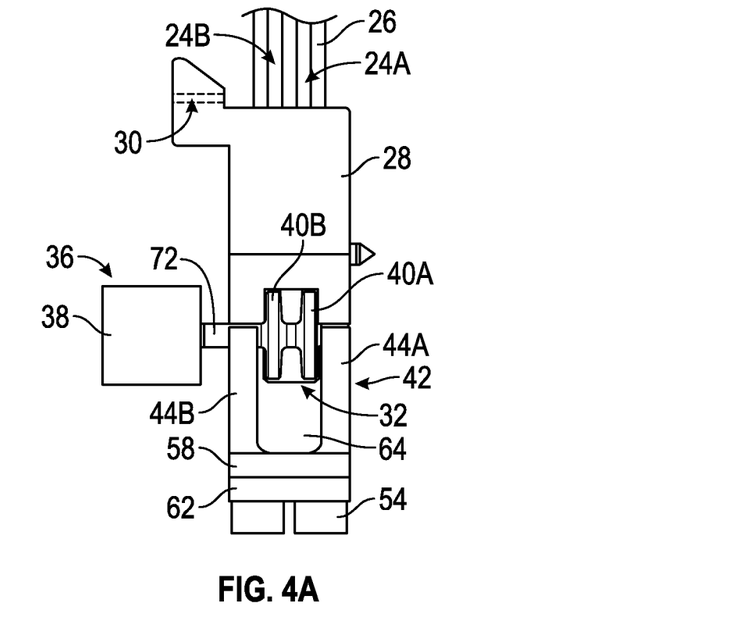
FIG. 4A illustrates a side view of a portion of the system, in accordance with at least one example of the present disclosure.
Figure 4B:
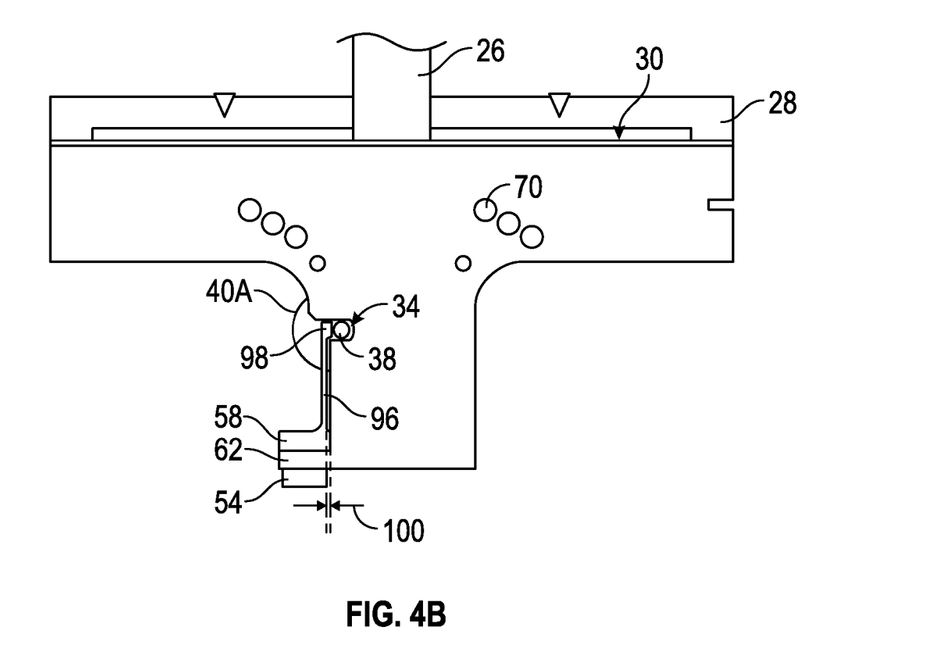
FIG. 4B illustrates a back view of the portion of the system of FIG. 4A, in accordance with at least one example of the present disclosure.

A difference between the thickness 57 of the extender portion 96 and the thickness 59 of the spacer portion 98 can be sufficient to provide a gap between the extender portion 96 and the side wall 64 of the cutting block 28, as illustrated in FIG. 4B. The gap can increase the ease of cleanability of the system and reduce the amount of material that may get trapped in the system.

FIG. 4A illustrates a side view of a portion of the system, in accordance with at least one example of the present disclosure. As illustrated in FIG. 4A, the circular guide members 40 are positioned within the longitudinal grooves 24. The resilient member 42 is coupled to the cutting block 28 via fasteners 54 extending through the plate portion 62 and to the base 58 of the resilient member 42. The legs 44 can extend from the base 58 and are configured to be in contact with the elongate body 72 of the roller 36. The circular guide members 40 can be positioned between the first leg 44A and the second leg 44B. As discussed herein, the friction between the circular guide members 40 and the longitudinal grooves 24, provided by the resilient member 42, enable the cutting block 28 to maintain a position along the depth arm 26. When the turn knob 38 is rotated, the circular guide members 40 can rotate within the longitudinal grooves 24 and can convert the rotational motion of turning the turn knob 38 into a linear motion that adjusts the cutting block 28 along the depth arm 26.

FIG. 4B illustrates a back view of the portion of the system of FIG. 4A, in accordance with at least one example of the present disclosure. The cutting block 28 can include slots 34 that can be configured to receive the elongate body 72 of the roller 36. As illustrated in FIG. 4B, the spacer portion 98 of the legs 44 can contact the elongate body 72 of the roller 36. The difference in thickness between the spacer portion 98 and the extender portion 96 can create a gap between the extender portion 96 and the side surface 64 of the cutting block 28. As discussed herein, the gap can increase the cleanability of the system. In an example, the gap can have a thickness of at least 0.50 millimeters.

Figure 5:
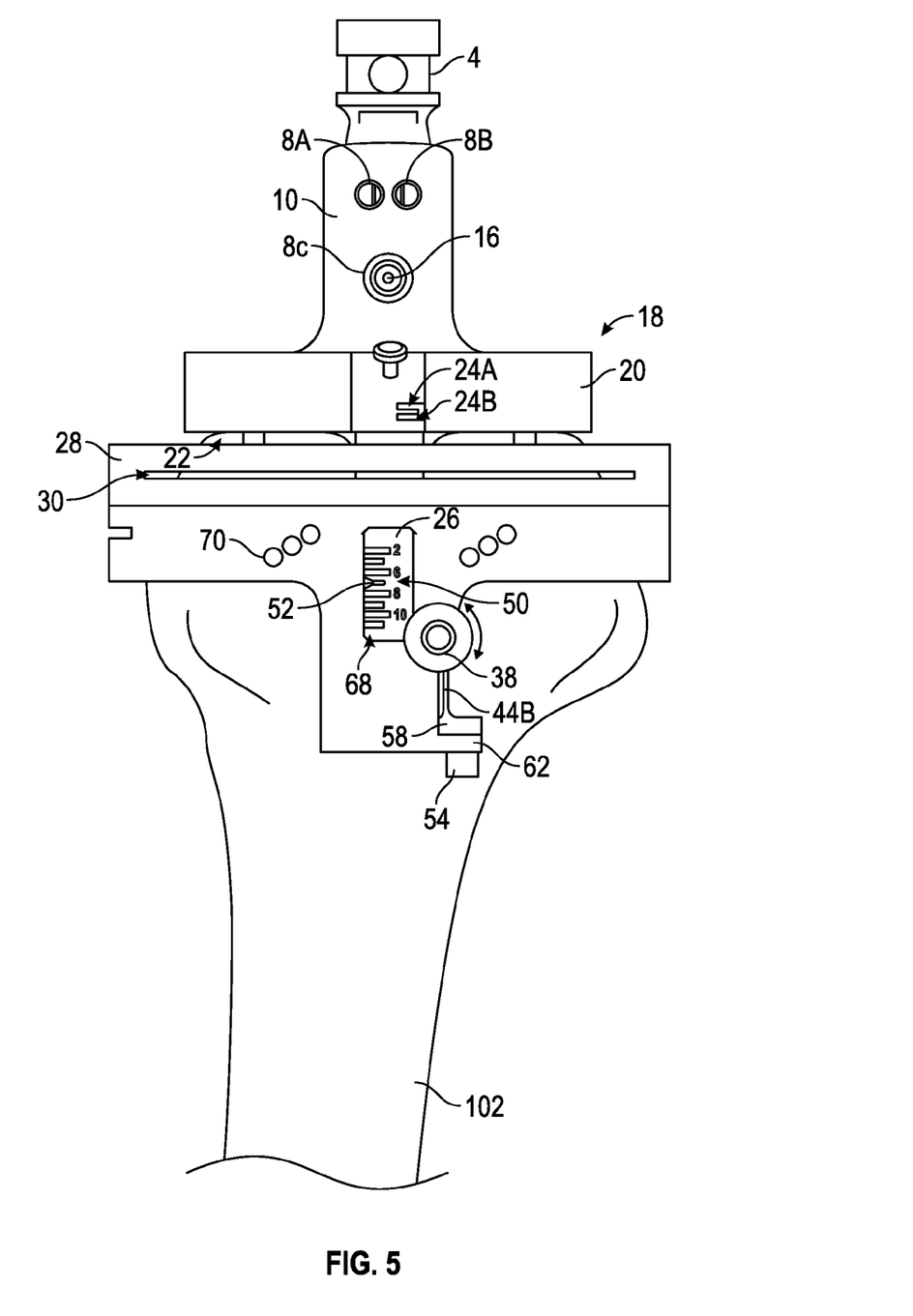
FIG. 5 illustrates a system being used in conjunction with a femur, in accordance with at least one example of the present disclosure.

FIG. 5 illustrates the system 2 being used in conjunction with a femur 102, in accordance with at least one example of the present disclosure. As illustrated in FIG. 5, the cutting block 28 is coupled to the depth arm 26 and the reference block 18 is coupled to the intramedullary rod or nail 4. In the example of FIG. 5, the varus/valgus angle of the cutting block 28 is at the minimum varus/valgus angle. For example, the locking 16 is inserted into varus/valgus angle hole 8C, which represents a minimum varus/valgus angle.

The turn knob 38 can be rotated to adjust the cutting depth of the slot. The turn knob 38 can be rotated in a first direction and a second direction to adjust the position of the cutting block 28 along the depth arm 26. For example, when the turn knob 38 is rotated to the right, the cutting depth of the slot 30 can decrease. When the turn knob 38 is rotated to the left, the cutting depth of the slot 30 can increase. The cutting block 28 can also include a depth gauge 52 that aligns with reference markings 50 on the depth arm 26 to indicate a cutting depth of the slot 30. The cutting block 28 can include locking holes 70 that are configured to receive locking pins to position the cutting block on the femur 108 at a particular depth and a particular varus/valgus angle.

Figure 6:
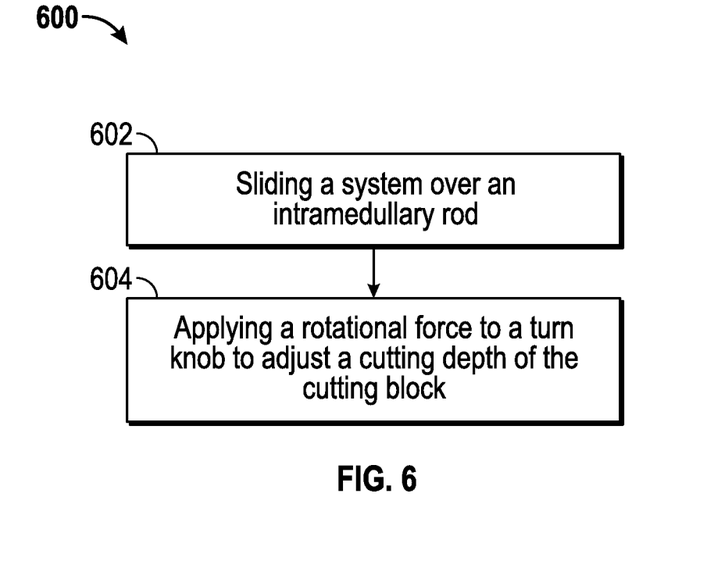
FIG. 6 illustrates a method of using a system, in accordance with at least one example of the present disclosure.

FIG. 6 illustrates a method 600 of using the system 2, in accordance with at least one example of the present disclosure. At 602, the method 600 can include sliding a system over an intramedullary rod or nail. The system can include a reference block, having a depth arm including a longitudinal groove, and a cutting block having an adjuster. The adjuster can include an elongate body having a turn knob and a circular guide member positioned along the elongate body.

At 604, the method 600 can include applying a rotational force to the turn knob to adjust a cutting depth of the cutting block. The circular guide member can rotates within the longitudinal groove in response to the rotational force. The method 600 can include adjusting the reference block with respect to the intramedullary rod to adjust a varus/valgus angle of the cutting block and coupling the reference block to the intramedullary rod. The method 600 can also include coupling the cutting block to a bone at a particular depth and a particular varus/valgus angle, and removing the reference block from the cutting block.

The above Detailed Description includes references to the accompanying drawings, which form a part of the Detailed Description. The drawings show, by way of illustration, specific embodiments in which the present surgical cutting block systems and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "varus/valgus angle" is used to refer to a varus angle only, a valgus angle only, or both a varus angle and a valgus angle.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system, comprising:
 a reference block including a body portion and a depth arm, the depth arm extending from the body portion and having at least one longitudinal groove extending along a side surface of the depth arm, the longitudinal groove including a first surface, a second surface opposite the first surface, and an edge located along the second surface;
 a cutting block having a longitudinal bore configured to receive the depth arm, the cutting block including a side opening that extends from an external surface of the cutting block to the longitudinal bore; and
 an adjuster configured to move and maintain a position of the cutting block along the depth arm, the adjuster, including:
  a roller having an elongate body, the roller including at least one circular guide member and a turn knob positioned along the elongate body, the at least one circular guide member including a first side surface and a second side surface opposing the first side surface, wherein at least a portion of the at least one circular guide member is configured to be positioned through the side opening of the cutting bock and within the at least one longitudinal groove; and
  a resilient member having a base configured to be coupled to the cutting block and at least one elongated resilient leg projecting from the base, wherein, when the base is coupled to the cutting block, the at least one elongated resilient leg directly engages and applies a force to the roller that secures the roller within the side opening of the cutting block and to the depth arm and allows rotation of the circular guide member within the longitudinal groove, the force is applied to the roller in a direction towards the depth arm such that a friction fit is formed between the edge and the second side surface of the circular guide member to couple the cutting block to the depth arm, and wherein, when the turn knob is rotated, the at least one circular guide member rotates within the at least one longitudinal groove to move the cutting block along the depth arm.

2. The system of claim 1, wherein the at least one elongated resilient leg includes an extender portion and a spacer portion, the spacer portion configured to contact the elongate body of the roller, and the extender portion located between the spacer portion and the base.

3. The system of claim 2, wherein the spacer portion has a first thickness and the extender portion has a second thickness, the first thickness greater than the second thickness.

4. The system of claim 3, wherein the first thickness of the spacer portion is sufficient to provide a gap between a side wall of the cutting block and the extender portion.

5. The system of claim 1, wherein the at least one circular guide member has a first hardness and the depth arm has a second hardness, the first hardness different from the second hardness.

6. The system of claim 5, wherein the first hardness is greater than the second hardness.

7. The system of claim 5, wherein the first hardness is less than the second hardness.

8. The system of claim 1, wherein the at least one longitudinal groove is a square groove in groove depth and groove width, such that the first surface and the second surface of the at least one longitudinal groove are parallel to each other.

9. The system of claim 8, wherein the first side surface of the at least one circular guide member is configured to be adjacent to the first surface of the at least one longitudinal groove and the second side surface of the at east one circular guide member is configured to be adjacent to the second surface of the at least one longitudinal groove.

10. The system of claim 9, wherein the first side surface of the at least one circular guide member is substantially perpendicular to a longitudinal axis of the roller and the second side surface of the at least one circular guide member forms an oblique angle relative to the longitudinal axis of the roller.

11. A system, comprising:
a reference block including a body portion and a depth arm, the depth arm extending from the body portion and having at least one longitudinal groove extending along a side surface of the depth arm; and
a cutting block coupled to the reference block, said cutting block having a slot, configured for guiding a cutting tool therethrough, a longitudinal bore configured to receive the depth arm, and a side opening that extends from an external surface of the cutting block to the longitudinal bore, and an adjuster, configured for moving and maintaining a position of the cutting block with respect to the reference block, the adjuster including:
a roller having an elongate body, the roller including:
at least one circular guide member, wherein at least a portion of the at least one circular guide member is configured to be positioned through the side opening of the cutting block and within the at least one longitudinal groove, and the at least one circular guide member is configured to move along the at least one longitudinal groove to move the cutting block with respect to the reference block; and
a turn knob, the at least one circular guide member and the turn knob positioned along the elongate body; and
a resilient member configured to apply a force to the roller to secure the roller within the side opening of the cutting block and to the depth arm, the resilient member including:
a base configured to be coupled to the cutting block; and
at least one elongated resilient leg projecting from the base, the at least one elongated resilient leg includes an extender portion and a spacer portion, wherein, when the base is coupled to the cutting block, the spacer portion is configured to directly engage the elongate body of the roller, and the extender portion located between the spacer portion and the base, the at least one elongated resilient leg applies a force to the roller in a direction towards the depth arm to frictionally couple the cutting block to the depth arm, the force securing the roller to the depth atm and allows rotation of the circular guide member within the longitudinal groove; and
a fastener configured to couple the resilient member to the cutting block,
wherein, when the turn knob is rotated, the at least one circular guide member rotates within the at least one longitudinal groove to move the cutting block along the depth arm.

12. The system of claim 11, wherein the spacer portion has a first thickness and the extender portion has a second thickness, the first thickness greater than the second thickness.

13. The system of claim 11, wherein the at least one circular guide member has a first hardness and the depth arm has a second hardness, the first hardness different from the second hardness.

14. The system of claim 11, wherein the at least one circular guide member includes a first surface and a second surface opposite the first surface, the first surface substantially perpendicular to a longitudinal axis of the roller and the second surface forming an oblique angle relative to the longitudinal axis of the roller.

* * * * *

UNITED STATES PATENT AND TRADEMARK OFFICE
CERTIFICATE OF CORRECTION

PATENT NO. : 9,622,755 B2
APPLICATION NO. : 13/726765
DATED : April 18, 2017
INVENTOR(S) : James S. Collins It is certified that error appears in the above-identified patent and that said Letters Patent is hereby corrected as shown below:

In the Claims

In Column 10, Line 61, in Claim 1, delete "bock" and insert --block-- therefor

In Column 11, Line 41, in Claim 9, delete "east" and insert --least-- therefor

In Column 11, Line 56, in Claim 11, delete "slot," and insert --slot-- therefor

In Column 12, Line 2, in Claim 11, delete "adjuster," and insert --adjuster-- therefor In Column 12, Line 35, in Claim 11, delete "atm" and insert --arm-- therefor Signed and Sealed this
Nineteenth Day of March, 2019

Andrei Iancu
*Director of the United States Patent and Trademark Office*